(12) United States Patent
Liu et al.

(10) Patent No.: US 8,329,879 B2
(45) Date of Patent: Dec. 11, 2012

(54) $H_3$LMN COMPOUND USED AS RADIOACTIVE AGENT FOR TREATMENT OF LIVER CANCER AND MANUFACTURING METHOD THEREOF

(75) Inventors: Show-Wen Liu, Shetou Township, Changhua County (TW); Cheng-Hsien Lin, Taipei (TW); Tsyh-Lang Lin, Bade (TW); Cheng-Fang Hsu, Toufen Township, Miaoli County (TW)

(73) Assignee: Atomic Energy Council-Institute of Nuclear Energy Research, Taoyuan County (TW)

( * ) Notice: Subject to any disclaimer, the term of this patent is extended or adjusted under 35 U.S.C. 154(b) by 482 days.

(21) Appl. No.: 12/558,911

(22) Filed: Sep. 14, 2009

(65) Prior Publication Data

US 2011/0065904 A1    Mar. 17, 2011

(51) Int. Cl.
*C07F 13/00* (2006.01)
(52) U.S. Cl. ............ 534/14; 534/10; 424/1.11; 424/1.65
(58) Field of Classification Search ............. 424/1.11, 424/1.65, 9.1, 9.2, 9.3, 9.4, 9.5; 534/7, 10–14; 564/1, 123, 305; 568/8, 303; 570/101
See application file for complete search history.

(56) References Cited

U.S. PATENT DOCUMENTS 7,067,508 B2 * 6/2006 Jeong et al. ............. 514/183
7,935,833 B2 * 5/2011 Liu et al. ................. 548/542

OTHER PUBLICATIONS

Magata et al (Bioconjugate Chemistry, 2004, vol. 15, No. 2, pp. 389-393).*

* cited by examiner

*Primary Examiner* — D L Jones
(74) *Attorney, Agent, or Firm* — Ming Chow; Sinorica, LLC

(57) ABSTRACT

$H_3$LMN series compounds used as radioactive agents for treatment of liver cancer and a manufacturing method thereof are revealed. 2-thioethylamine hydrochloride is reacted with triphenylmethanol for protection of thiol to obtain 2-[(triphenylmethyl)thio]ethylamine. Then obtain N-[2-((triphenylmethyl)thio)ethyl]chloroacetamide by a transamidation reaction between 2-[(triphenylmethyl)thio]ethylamine and chloroactyl chloride. Next produce a amine-amide-thiol ligand-N-[2-((triphenylmethyl)thio)ethyl][2-((triphenylmethyl)thio)ethylamino]acetamide by a substitution reaction of N-[2-((triphenylmethyl)thio)ethyl]chloroacetamide and 2-[(triphenylmethyl)thio]ethylamine. After respective reaction with 1-bromotetradecane, 1-bromohexadecane and ethyl 16-bromohexadecanoate, $H_3$LMN series compounds are obtained. These amine-amide-dithiols quadridentate ligands can react with $MO^{3+}$ (M=Tc or Re) to produce electrically neutral complexes. The complexes have high lipophilicity, allowing them soluble in lipiodol to be applied to radiation therapy for liver cancer.

8 Claims, 5 Drawing Sheets

H₃LMN-16 (C16)

- ReO(PPh₃)₂Cl₃(C19)
- Triethylamine(C3)
- Methanol(C20)

ReOMN-16

(C21)

H₃LMN-16ET (C18)

1. ReO(PPh₃)₂Cl₃(C19)
2. Triethylamine(C3)
3. Methanol(C20)

ReOMN-16ET

(C22)

$H_3LMN$ COMPOUND USED AS RADIOACTIVE AGENT FOR TREATMENT OF LIVER CANCER AND MANUFACTURING METHOD THEREOF

BACKGROUND OF THE INVENTION

1. Field of Invention

The present invention relates to a precursor of a radioactive agent for treatment of liver cancer and a manufacturing method thereof, especially to $H_3LMN$ series compounds applied to radiation therapy for liver cancer and a manufacturing method thereof.

2. Description of Related Art

Liver cancer is one of the most common causes of death nowadays. According to data from Department of Health, R.O.C, 7809 people died for liver cancers in 2007. Thus the prevention and therapy of liver cancers are important issues in domestic medical research. Conventional ways of treatment for hepatoma includes surgery, chemical therapy and radiation therapy. However, the overall cure rate remains unsatisfied. There is an urgent need to find out other effective alternatives.

Lipiodol is an iodized Poppy-seed oil. Domestic or foreign studies all demonstrate that liver cancer tissues have significant intake of lipiodol. Some researchers tried to label lipiodol with radioisotope such as I-131, Y-90 and Re-188 so as to get therapeutic agents used for radiation therapy of liver cancers. In European, $^{131}$I-Lipidol is available for liver cancer therapy. Yet the iodine-131 emits high energy gamma rays and delivers a higher total dose. Moreover, the I-131 is expensive. Thus its applications are limited. As to rhenium-188, it is a nuclide that emits both beta ($\beta$max=2.12 Mev) and gamma rays ($\gamma$=155 KeV) and having a half-life of 16.9 h. Rhenium-188 is a very potential radioisotope for disease diagnosis and therapy because Re-188 is a generator-produced radioisotope easy to be obtained, with proper radioactive energy and short half-life. It is expected Re-188 will play an important role in radiation therapy for cancer. Therefore, lipiodol with Re-188 may be an effective therapeutic agent for radiation therapy of liver cancers.

$^{188}$Re-DD has high lipophilicity and initial uptake in liver cancer is high. However, retention of $^{188}$Re-DD in liver tumors is low. This can be explained by a paper—Y. S. Lee, J. M. Jeong, Y. J. Kim, et al., Nucl. Med. Commu., 23, 237-242 (2002), through a proton transfer, $^{188}$Re-DD in cell fluid forms a cation that is hydrophilic and is easy to be released from cells, as shown in FIG. 1. Thus the retention of $^{188}$Re in liver cancer cells is far more less than expected.

Moreover, refer to C. H. Lin, F. L. Liao, S. L. Wang., Synth. React. Inorg. Met.-Org. Chem. 27(8), 1167-1182 (1997), after complex reaction of N-(1-carboethoxy-2-thioethyl)[N-(2-thioethyl)amino]aceta-mide ($H_4L$) with $ReO(PPh_3)_2Cl_3$, two compounds are obtained. As shown in FIG. 2, ReOHL is electrically neutral while ReOL is an anion carrying a negative charge. Obviously, ReOL is resulted from loss of a proton of ReOHL. Based on this experiment, it is believed that $^{188}$Re-DD in body fluid may lose a proton to yield a water-soluble anion.

Thiols are also relatively easy to oxidize under neutral or alkaline conditions, especially dithiol molecules. Oxidation of the thiol group yields a disulfide (S—S) bond. Once the S—S bond forms, there is no formation of a S-M (M=Tc or Re) bond. That means the thiol groups are unable to be applied to preparation of therapeutic agents for liver cancer. DADT (diamide dithiol) and BAT (bis-aminoethanethiol) are frequently used organic ligands that bind with technetium (Tc) or rhenium (Re) to form complexes (coordination compounds), as shown in FIG. 3A and FIG. 3B (M=Tc or Re).

Thus the compounds of the present invention can release three protons from amines, amides and thiols during complex reactions with $MO^{3+}$ (M=Tc or Re) and the complexes formed are electrically neutral. Such complexes with good lipophilicity resulted from long-chain alkyl group contained are easily soluble in lipiodol. Therefore, the complexes can be used as effective radioactive therapeutic agents for liver cancers.

SUMMARY OF THE INVENTION

Therefore it is a primary object of the present invention to provide $H_3LMN$ series compounds applied to radioactive agents for treatment of liver cancer and a manufacturing method thereof. The manufacturing method is to bind with a long chain alkyl group such as a tetradecyl group, a hexadecyl group, or hexadecyl carboxylic acid ethyl ester so as to make Re or Tc complexes have high lipophilicity and become soluble. Thus the retention of radioactive agents in liver cancer cells is increased.

It is another object of the present invention to provide $H_3LMN$ series compounds applied to radioactive agents for treatment of liver cancer and a manufacturing method thereof in which $CPh_3$ is used as a protecting group for thiol group to prevent oxidation of thiol group that results in no complex reactions with Tc or Re. And the compounds have stable chemical properties.

In order to achieve above objects, the present invention provide $H_3LMN$ series compounds applied to radioactive agents for treatment of liver cancer and a manufacturing method thereof. The complexes formed between $H_3LMN$ series ligands and Tc/Re are soluble in lipiodol so that they can be applied to radiation therapy for liver cancer. The method is as following: use amine-amide-dithiols as a basic structure of quadridentate ligands and make their Tc or Re complexes become electrically neutral. The amino group of the ligand is bound with a long chain alkyl group such as a tetradecyl group, a hexadecyl group, or hexadecyl carboxylic acid ethyl ester so as to increase its solubility in lipiodol. Moreover, a trityl group is used as a protecting group for thiol group. These amine-amide-dithiols quadridentate ligands react with $MO^{3+}$ (M=Tc or Re) to produce electrically neutral complexes. A protecting group helps to prevent oxidation of the thiol group in $N_2S_2$ ligand for easy storage and the protecting group is released easily during the complex reactions. The Tc or Re complexes have high lipophilicity due to the binding between the amino group and the long chain alkyl group such as a tetradecyl group, a hexadecyl group, or hexadecyl carboxylic acid ethyl ester and become soluble in lipiodol. Thus the organic ligands-$H_3LMN$ series compounds can be labeled with Tc or Re and to be applied to radiation therapy for liver cancer together with lipiodol.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

In the present invention, when DADT reacts with $MO^{3+}$ (M=Tc or Re), four protons are released from two amides and two thiols groups so that the complex formed is an anion while only three protons are released during complex reaction of BAT with $MO^{3+}$ (M=Tc or Re) and the complex is electrically neutral.

As to a ligand AADT (monoamine-monamide dithiol) having an amine, an amide and two thiols synthesis in the present invention, three protons are released from amide and thiol to form electrically neutral complex during its reaction with $MO^{3+}$ (M=Tc or Re). Or four protons are released from amine, amine, amide and thiol to form an anion complex. Based on above results, a $N_2S_2$ ligand having a tertiary amine, an amide and two thiols is synthesized according to the present invention. The $N_2S_2$ ligand can react with $MO^{3+}$ (M=Tc or Re) to form electrically neutral complexes. The ligand contains only three free protons to be released and reacts with $ReO^{3+}$ to form stable complexes. The complexes contain long chain alkyl groups and have good lipophilicity to be soluble in lipiodol so as to be applied to research and radiation therapy for liver cancer.

Furthermore, the thiol group is protected against oxidation and common protecting groups include $COC_6H_5$, $CH_2C_6H_4OCH_3$, $CPh_3$, etc. The protecting group for the thiol group must be removed before complex reactions. For example, $COC_6H_5$ is a protecting group for $MAG_3$ (MercaptoAcetyl Tri Glycine). Before complex reactions, $MAG_3$ is hydrolyzed in alkaline solutions so as to remove the protecting group. In the present invention, $CPh_3$ is used as a protecting group for thiol group while $CPh_3$ is released easily during complex reactions. Thus there is no need to remove this protecting group in advance and this allows convenient use of the bifunctional compounds.

Figure 1:
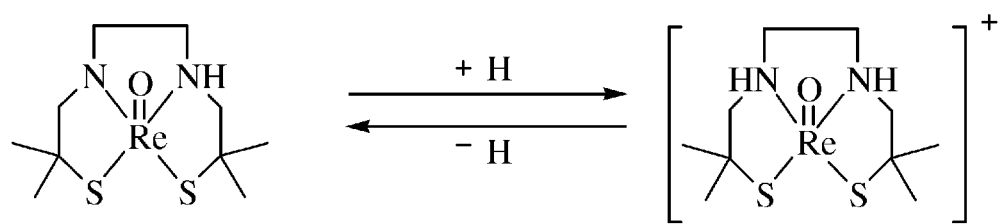
FIG. 1 is a reaction equation showing formation of a cation from $^{188}$Re-DD through a proton transfer in conventional techniques.
Figure 2:
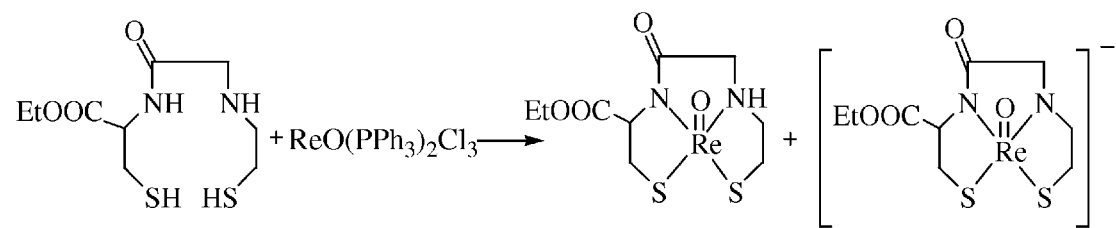
FIG. 2 is a reaction equation showing a complex reaction of N-(1-carboethoxy-2-thioethyl)[N-(2-thioethyl)amino]acetamide ($H_4L$) and $ReO(PPh_3)_2Cl_3$ in conventional techniques.
Figure 3A:
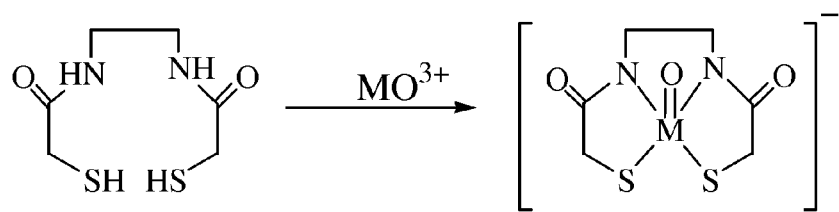
FIG. 3A to FIG. 3C are reaction equations showing $N_2S_2$ ligands and formation of complexes (M=Tc or Re) in conventional techniques.
Figure 3B:
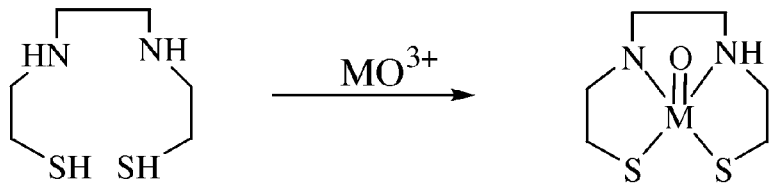
Figure 3C:
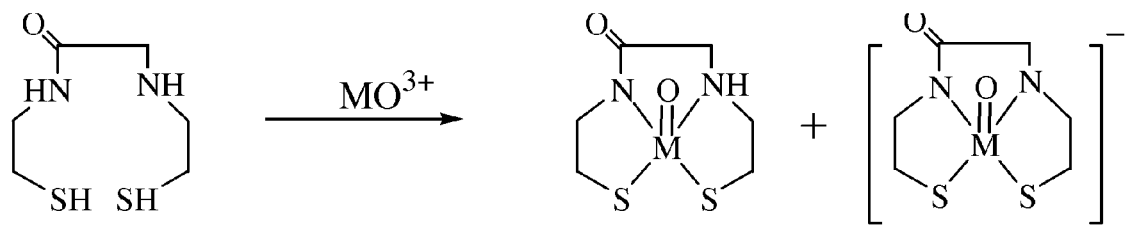
Figure 4A:
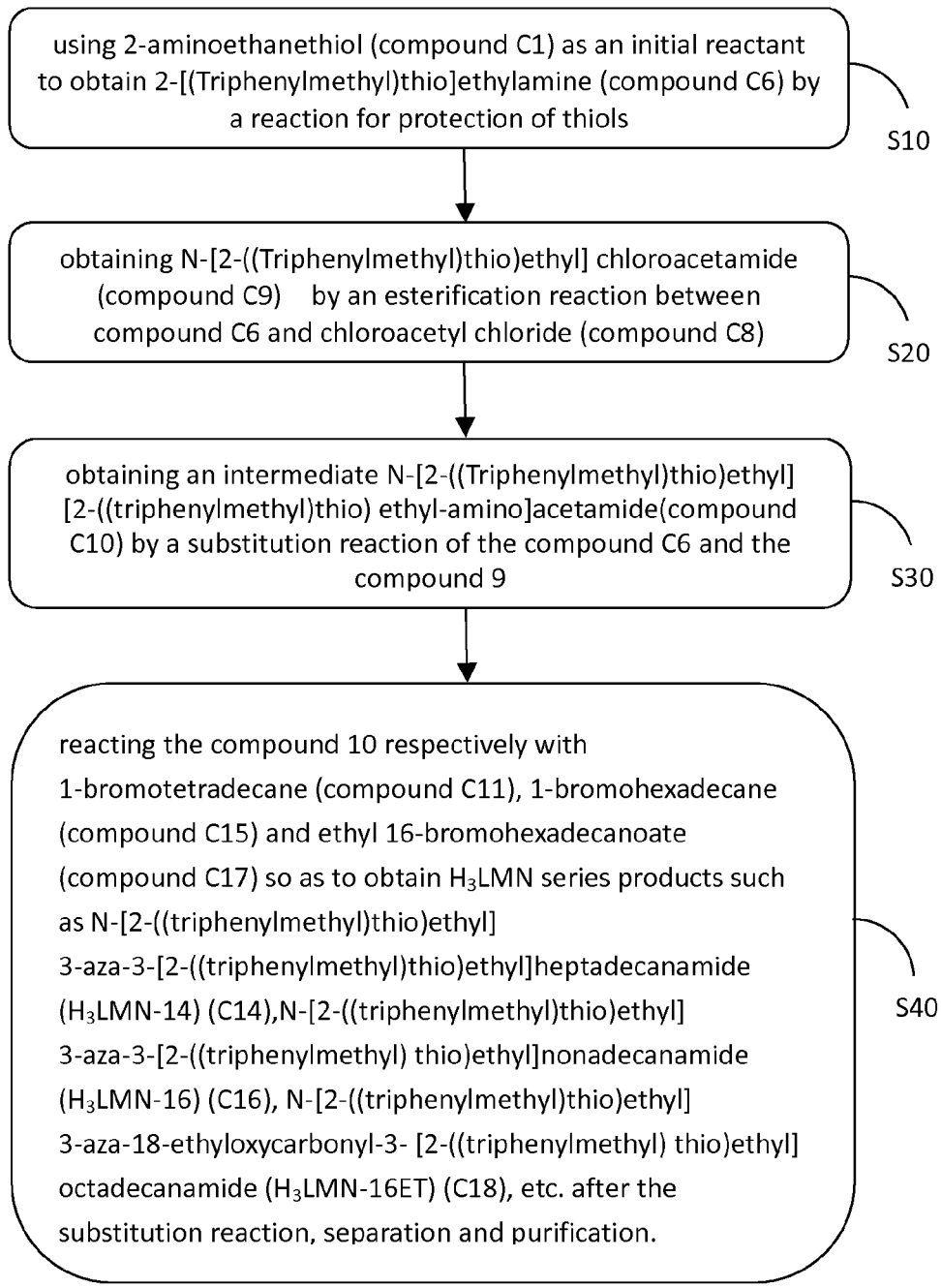
FIG. 4A is a flow chart showing manufacturing of $H_3LMN$ series compounds according to the present invention.
Figure 4B:
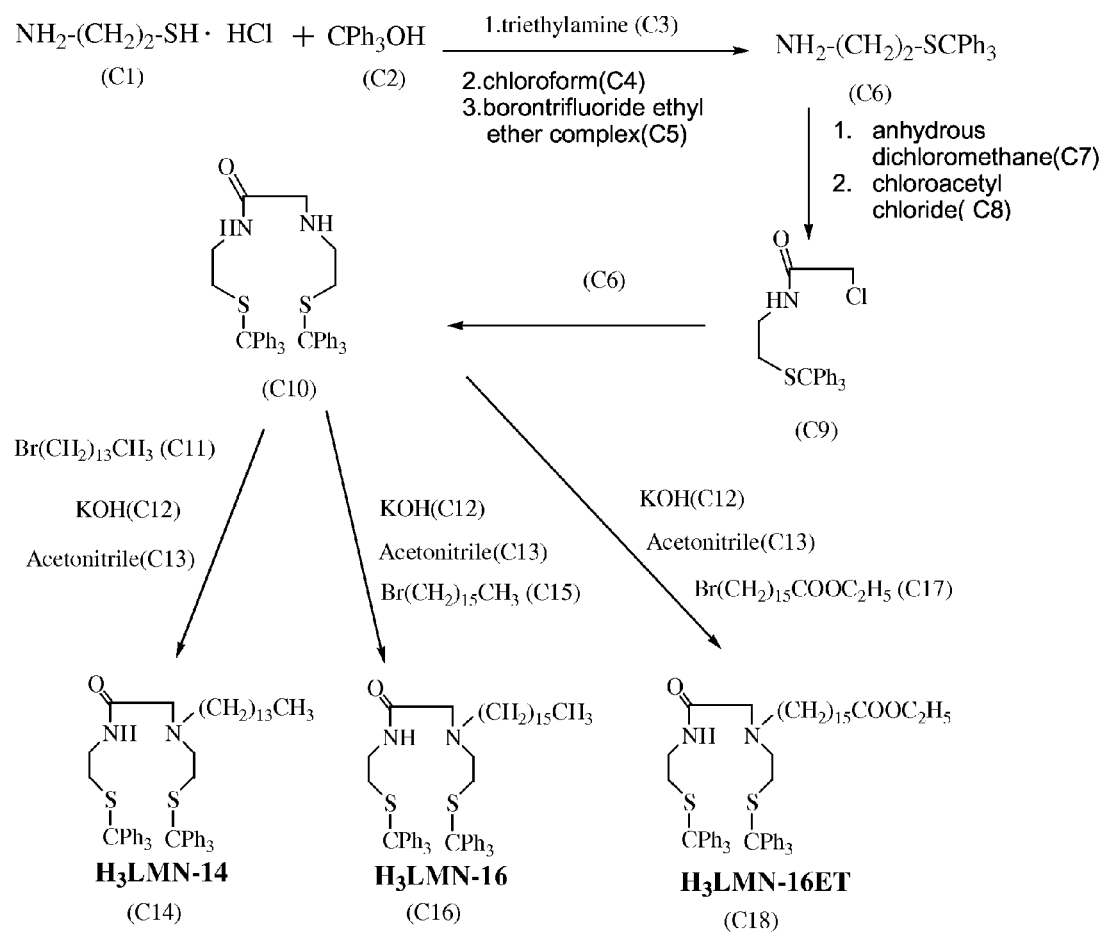
FIG. 4B shows reaction equations of $H_3LMN$ series compounds $H_3LMN$ series compounds according to the present invention.

Refer to FIG. 4A and FIG. 4B, a flow chart showing manufacturing steps and a reaction equation of an embodiment according to the present invention are revealed. A manufacturing method of a precursor of a radioactive agent for treatment of liver cancer includes the following steps:

Step S10: using 2-aminoethanethiol (compound C1) as an initial reactant to obtain 2-[(Triphenylmethyl)thio]ethylamine (compound C6) by a reaction for protection of thiols;

Step S20: obtaining N-[2-((Triphenylmethyl)thio)ethyl]chloroacetamide (compound C9) by an esterification reaction between compound C6 and chloroacetyl chloride (compound C8);

Step S30: obtaining an intermediate N-[2-((Triphenylmethyl)thio)ethyl][2-((triphenylmethyl)thio)ethyl-amino]acetamide (compound C10) by a substitution reaction of the compound C6 and the compound 9; and Step S40: reacting the compound 10 respectively with 1-bromotetradecane (compound C11), 1-bromohexadecane (compound C15) and ethyl 16-bromohexadecanoate (compound C17) so as to obtain $H_3LMN$ series products such as N-[2-((triphenylmethyl)thio)ethyl]3-aza-3-[2-((triphenylmethyl)thio)ethyl]heptadecanamide ($H_3LMN$-14) (C14), N-[2-((triphenylmethyl)thio)ethyl]3-aza-3-[2-((triphenylmethyl)thio)ethyl]nonadecanamide ($H_3LMN$-16) (C16), N-[2-((triphenylmethyl)thio)ethyl]3-aza-18-ethyloxycarbonyl-3-[2-((triphenylmethyl)thio)ethyl]octadecanamide ($H_3LMN$-16ET) (C18), etc. after the substitution reaction, separation and purification.

The $H_3LMN$ compound described as following:

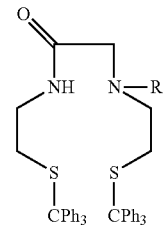

$H_3LMN$ series compounds (such as compound C14, compound C16 and compound C18) are amine-amide-dithiols quadridentate ligands. While chelating with $MO^{3+}$, the $H_3LMN$ series compounds release three protons to form electrically neutral compounds-MO—$H_3LMN$. The M atom in the $MO^{3+}$ is selected from one of the followings: Tc-99, Tc-99m, Tc-95m, Re-186 and Re-188. The complex MO—$H_3LMN$ has no free proton to be released and without ability to receive protons. That means no matter under what conditions, the complex MO—$H_3LMN$ is unable to be converted into a hydrophilic anion or cation. Such character improves retention of MO—$H_3LMN$ in liver cancer cells. Moreover, long chain alkyl groups increase lipophilicity of MO—$H_3LMN$ and improve the solubility of MO—$H_3LMN$ in lipiodol so as to achieve optimal retention in liver cancer cells.

For removing the protecting group-$CPh_3$ for the thiol group, dissolve $H_3LMN$ is in trifluroacetic acid and add excess amount of triethylsilane. Thus $CPh_3$ is released from thiol and solid precipitate insoluble in trifluroacetic acid is formed. The precipitate is obtained by filtering or washing with hexane. This is easy and convenient.

Once $H_3LMN$ reacts with Re or Tc to form complexes, there is no need to remove the protecting group for thiol in advance. $H_3LMN$ directly reacts with Re or Tc to form Re complexes or Tc complexes while the protecting group for thiol-$CPh_3$ is released easily during the complex reactions. As to Re complexes or Tc complexes, they are electrically neutral, lipophilic and easy soluble in lipiodol. Thus these complexes can be labeled with Re-188 and then is dissolved in lipiodol to be applied to researches of liver cancers.

In the step S10, for synthesis of 2-[(Triphenylmethyl)thio] ethylamine (compound C6), take 5 g (44.0 mmol) 2-thioethylamine hydrochloride (compound C1), 11.5 g (44.0 mmol) triphenylmethanol (compound C2) and 7.4 mL (52.8 mmol) triethylamine (compound C3), all dissolve in 80 mL chloroform (compound C4). After being heated and refluxed, slowly drop catalyst –14.9 mL (118.8 mmol) borontrifluoride ethyl ether complex (compound C5) into solution and continue heating under reflux for 4 hours. After cooling down, wash with water solution of sodium bicarbonate (2×100 mL). The organic phase is dehydrated by $Na_2SO_4$ and then is concentrated under reduced pressure so as to obtain the product-compound C8 (14g, 99%).

Analysis of the synthesis product-compound C6: IR (neat) ν 3381 ($NH_2$) $cm^{-1}$. $^1H$ NMR ($CDCl_3$) δ 7.42 (m, 3 H, Ph), 7.30 (m, 12 H, Ph), 2.58 (t, J=6.6 Hz, 2 H, $CH_2N$), 2.32 (t, J=6.6 Hz, 2 H, $CH_2S$), 1.45 (br, 2 H, $NH_2$). $^{13}C$ NMR ($CDCl_3$) δ 144.80, 192.52, 127.81 and 126.60 (Ph), 66.51 (CPh), 40.94 ($CH_2N$), 36.09 ($CH_2S$). MS m/z 319 ($M^+$), 243 ($M^+$-$C_6H_5$+1).

In the step S20, N-[2-((Triphenylmethyl)thio)ethyl]chloroacetamide (compound C9) is synthesized by followings: dissolve the compound C6(9.2 g, 28.9 mmol) and triethylamine (compound C3) (4.8 mL, 34.7 mmol) in 100 mL anhydrous dichloromethane (compound C7). In an ice bath, slowly drop 2.8 mL (34.7 mmol) chloroacetyl chloride (compound C8) that is dissolved in 10 mL anhydrous dichloromethane (compound C7) into the above solution. After finishing dropping, stir the solution for 2 hours at room temperature. Then wash with following liquids in turn: an aqueous solution of hydrogen chloride, and an aqueous solution of sodium carbonate. The organic phase is dehydrated by $Na_2SO_4$ and then is concentrated under reduced pressure so as to obtain compound C9 (11.2g, 97.7%).

Analysis of the synthesis product-compound C9: IR (neat) ν 3413 and 3306 (NH), 1662 (CO) $cm^{-1}$. $^1H$ NMR ($CDCl_3$) δ 7.41 (m, 3 H, Ph), 7.24 (m, 12 H, Ph), 6.48 (br, 1 H, NH), 3.97 (s, 2 H, $CH_2Cl$), 3.12 (q, J=6.3 Hz, 2 H, $CH_2N$), 2.43 (t, J=6.3 Hz, 2 H, $CH_2S$). $^{13}C$ NMR ($CDCl_3$) δ 165.63 (CO), 144.47, 129.48, 127.97 and 126.81 (Ph), 66.52 (CPh), 42.54 ($CH_2Cl$), 38.35 ($CH_2N$), 31.67 ($CH_2S$). MS m/z 397 and 395 ($M^+$), 243 (($CPh_3)^+$).

In the step S30, for synthesis of the compound C10 N-[2-((Triphenylmethyl)thio)ethyl][2-((triphenylmethyl)thio)ethyl-amino]acetamide, dissolve the compound C9 (11.2 g, 28.3 mmol) and the compound C6 (9.0 g, 28.3 mmol) in 100 mL anhydrous dichloromethane (compound C7), add 6 mL (42.5 mmol) triethyamine (compound C3) and then the solution is heated under reflux for three days. After cooling down, wash with aqueous solution of sodium bicarbonate and take an organic layer. The organic phase dehydrated and concentrated by $Na_2SO_4$. By a separation and purification technique-liquid chromatography($SiO_2$, ethylacetate:hexane=1:1), the product C10 (13.8 g, 72%) is obtained.

Analysis of the synthesis product-compound C10: IR (neat) ν 3330 (NH), 1670 (CO) $cm^{-1}$. $^1H$ NMR ($CDCl_3$) δ 7.42 (m, 4 H, HNCO and Ph), 7.20 (m, 12 H, Ph), 3.07 (m, 4 H, $CH_2NCO$ and $CH_2CO$), 2.38 (m, 6 H, $CH_2NHCH_2CO$ and $CH_2S$), 1.94 (br, 1H, $NHCH_2CO$). $^{13}C$ NMR ($CDCl_3$) δ 170.84 (CO), 144.61, 129.47, 127.88 and 126.69 (Ph), 66.72 and 66.65 ($CPh_3$), 51.62 ($CH_2CO$), 48.19 ($CH_2NHCH_2CO$), 37.70 ($CH_2NHCO$), 32.12 and 31.97 ($CH_2S$). MS m/z 243 (($CPH_3)^+$).

In the step S40, for synthesis of the compound C14-N-[2-((Triphenylmethyl)thio)ethyl]3-aza-3-[2-((triphenylmethyl)thio)ethyl]nonadecanamide ($H_3LMN$-14), dissolve the compound C10 (3.2 g, 4.2 mmol), 2.3 mL (8.4 mmol) 1-bromotetradecane (compound C11) and 0.3 g (5.0 mmol) potassium hydroxide (KOH, compound C12) in 60 mL acetonitrile (compound C13) and heat under reflux for 24 hours. After vacuum filtration, collect the filtrate. Then the filtrate is concentrated under reduced pressure and is treated by liquid chromatography ($SiO_2$, ethyl acetate:hexane=1:1), a separation and purification technique so as to obtain the product C14, $H_3LMN$-14 (1.6 g, 43.2%).

Analysis of the synthesis product-compound C14: IR (neat) ν 3350 (NH), 1681 (CO) $cm^{-1}$. $^1H$ NMR ($CDCl_3$) δ 7.22-7.16 (m, 31 H, NH and Ph), 3.0 (q, J=6.3 Hz, 2 H, C$H_2NH$), 2.84 (S, 2 H, $CH_2CO$), 2.41-2.20 (m, 8 H, $CH_2S$ and $\overline{C}OCH_2N(CH_2)_2$), 1.26 (m, 22 H, $(CH_2)_{11}CH_3$), 0.88 (t, J=6.9 Hz, 3 H, C$\overline{H_3}$). $^{13}C$ NMR ($CDCl_3$) $\overline{\delta}$ 171.23 (CO), 144.73, 144.69, 129.49, 127.85, 126.63 and 126.61 (Ph), 66.69 and 66.63 (CPh), 58.23, 54.82, 53.78, 37.87, 31.95, 31.88, 29.97, 29.66, 29.61, 29.47, 27.27, 22.65 ($CH_2$), 14.09 ($CH_3$). MS m/z 243 (($CPh_3)^+$).

In the step S40, for synthesis of the compound C16, N-[2-((Triphenylmethyl)thio)ethyl]3-aza-3-[2-((triphenylmethyl)thio)ethyl]nonadecanamide ($H_3LMN$-16), dissolve the compound C10 (3.4 g, 5.0 mmol), 6.2 g (20.3 mmol) 1-bromohexadecane (compound C15) and 0.34 g (6.1 mmol) potassium hydroxide (KOH, compound C12) in 80 mL acetonitrile (compound C13) and heat under reflux for 72 hours. After filtering and concentration under reduced pressure, the filtrate is separated and purified by liquid chromatography ($SiO_2$, ethyl acetate:hexane=1:4) so as to obtain the product C16, $H_3LMN$-16 (3.2 g, 70%).

Analysis of the synthesis product-compound C16:IR (neat) ν 3350 (NH), 1681 (CO) $cm^{-1}$. $^1H$ NMR ($CDCl_3$) δ 7.22-7.16 (m, 31 H, NH and Ph), 3.0 (q, J=6.3 Hz, 2 H, C$H_2NH$), 2.84 (S, 2 H, $CH_2CO$), 2.41-2.20 (m, 8 H, $CH_2S$ and $\overline{C}OCH_2N(CH_2)_2$), 1.26 (m, 28 H, $(CH_2)_{14}CH_3$), 0.88 (t, J=6.9 Hz, 3 H, C$\overline{H_3}$). $^{13}C$ NMR ($CDCl_3$) $\overline{\delta}$ 171.21 (CO), 144.71, 144.68, 129.50, 127.85, 126.64 and 126.61 (Ph), 66.72 and 66.63 (CPh), 58.18, 54.79, 53.76, 37.88, 31.91, 31.88, 29.66, 29.62, 29.46, 29.31, 27.25, 22.64 ($CH_2$), 14.09 ($CH_3$). MS m/z 243 (($CPh_3)^+$).

In the step S40, for synthesis of the compound C18, N-[2-((Triphenylmethyl)thio)ethyl]3-aza-19-ethyloxycarbonyl-3-[2-((triphenylmethyl)thio)ethyl]octadecanamide ($H_3LMN$-16ET), dissolve the compound C10 (3.6 g, 4.8 mmol), ethyl 16-bromohexadecanoate (compound C17, 2.1 g, 5.8 mmol) and the compound C12 potassium hydroxide (KOH, 0.34g, 6.1 mmol) in 80 mL acetonitrile (compound C13) and heat under reflux for 48 hours. After filtering and concentration under reduced pressure, the filtrate is separated and purified by liquid chromatography ($SiO_2$, ethyl acetate:hexane=1:4) so as to obtain the oily product C18, $H_3LMN$-16ET (2.4 g, 48%).

Analysis of the synthesis product-compound C18: IR (neat) ν 3349 (NH), 1734 and 1681 (CO) $cm^{-1}$. $^1H$ NMR ($CDCl_3$) δ 7.25-7.18 (m, 31 H, NH and Ph), 4.10 (q, J=7.2 Hz, $CH_2CH_3$), 3.0 (q, J=6.3 Hz, 2 H, $CH_2NH$), 2.83 (S, 2 H, C$\overline{H}_2CON$), 2.30-2.20 (m, 10 H, $\overline{C}H_2S$, $SCH_2CH_2N$, $CH_2CH_2CH_2N$ and $CH_2COOEt$), 1.61 (m, 2 H, $C\overline{H}_2C$ $H_2CH_2N$), 1.24 (m, 31 H, $CH_2CH_2(CH_2)_{12}CH_2COOCH_2C$ $\overline{H}_3$). $^{13}C$ NMR ($CDCl_3$) δ 173.82 and $\overline{1}$71.22 (CO), 144.70, 144.65, 129.47, 127.81, 127.52, 126.59 and 126.57 (Ph), 66.66 and 66.60 (CPh), 60.05, ($CH_2CH_3$), 58.18, 54.79, 53.75, 37.84, 34.30, 31.90, 29.92, $2\overline{9}$.58, 29.43, 29.39, 29.19, 29.07, 27.24, 26.98, 24.90 ($CH_2$), 14.17 ($CH_3$). MS m/z 243 (($CPh_3)^+$).

Figure 5:
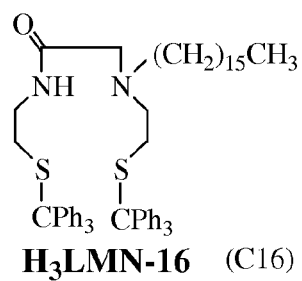
FIG. 5 is a reaction equation showing $H_3LMN$-16 reacting with Re according to the present invention.
Figure 5:
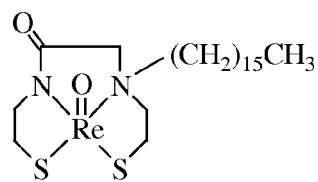

Furthermore, an embodiment of chelation reactions of $H_3LMN$ series compounds with $MO^{3+}$ is revealed. Refer to FIG. 5, synthesis of the compound C21, [N-(2-Thioethyl)3-aza-3-(2-thioethyl)nonadecanamido]oxorhenium(V) (ReOLMN-16) is used as an example. Dissolve compound $H_3LMN$-16 (compound C16, 0.68 g, 0.76 mmol), ReO$(PPh_3)_2$ $Cl_3$ (compound C19, 0.76 g, 0.9 mmol) and triethylamine (compound C3, 0.38 g, 3.8 mmol) in 50 mL methanol (compound C20) and heat overnight at 55° C. After filtering, the reaction solution is dried under reduced pressure. Dissolve residues with 30 mL chloroform (C4), wash with 30 mL water and dehydrate by adding anhydrous sodium sulfate. After being concentrated under reduced pressure, the mixture is separated and purified by liquid chromatography ($SiO_2$, ethyl acetate:hexane=1:2) so as to obtain the sorrel oily product C21, ReOLMN-16 (93.8 mg, 20%).

Analysis of the synthesis product-compound C21: IR (neat) ν 1664 (CO), 967 (ReO) $cm^{-1}$. $^1H$ NMR ($CDCl_3$) δ 4.64 (d, J=16.5 Hz, 1 H, $CH_2CO$), 4.56 (dd, J=3.9 and 1.2 Hz, 1 H, $CH_2NCO$), 4.12 (d, J=16.5 Hz, 1 H, $CH_2CO$), 4.06 (m, 1 H, $CH_2CH_2NCO$), 3.86 (m, 1 H, $CH_2(CH_2)_{14}CH_3$), 3.48 (m, 1 H, $CH_2(CH_2)_{14}CH_2$), 3.35 (m, 1 H, $CH_2CH_2NCH_2CO$), 3.21 (m, 3 H, $CH_2CH_2NCOCH_2NCH_2CH_2S$), 2.86 (dd, J=13.8 and 4.8 Hz, 1 H, $SCH_2CH_2NCH_2CO$), 1.78 (m, 2 H, $CH_2CH_2CH_2N$), 1.58 (m, 1 H, $SCH_2CH_2NCH_2CO$), 1.40-1.20 (m, 26 H, $(CH_2)_{13}CH_3$), 0.88 (t, J=6.6 Hz, 3 H, $CH_3$). $^{13}C$ NMR ($CDCl_3$) δ 187.07 (CO), 67.05, 63.94, 63.88, 59.77, 47.76, 38.81, 31.89, 29.62, 29.54, 29.42, 29.36, 29.32, 29.21, 26.77, 23.60 and 22.65 ($CH_2$), 14.09 ($CH_3$). MS m/z 618 and 616 ($M^+$).

Figure 6:
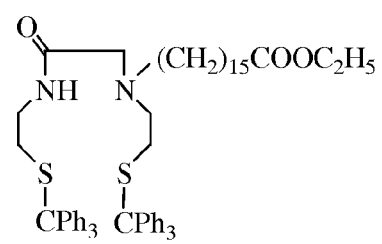
FIG. 6 is a reaction equation showing $H_3LMN$-16ET reacting with Re according to the present invention.
Figure 6:
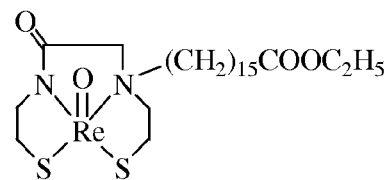

In addition, another embodiment of chelation reactions of $H_3LMN$ series compounds with $MO^{3+}$ is revealed. Refer to FIG. 6, synthesis of the compound C22, [N-(2-Thioethyl)3-aza-19-ethyloxycarbonyl-3-(2-thioethyl)octadecanamido] oxorhenium(V) (ReOLMN-16ET) is used as an example. Dissolve compound $H_3LMN$-16ET (C18, 0.77 g, 0.8 mmol), $ReO(PPh_3)_2Cl_3$ (C19, 0.76 g, 0.9 mmol) and triethylamine (C3, 0.38 g, 3.8 mmol) in 50 mL methanol (compound C20) and heat overnight at 55° C. After filtering, the reaction solution is dried under reduced pressure. Dissolve residues with 30 mL chloroform (C4), wash with 30 mL water and dehydrate by adding anhydrous sodium sulfate. After being concentrated under reduced pressure, the mixture is separated and purified by liquid chromatography ($SiO_2$, ethyl acetate:hexane=1:2) so as to obtain the sorrel oily product C22, ReOLMN-16ET(119 mg, 22%).

Analysis of the synthesis product-compound C22: IR (neat) ν 1733 and 1662 (CO), 968 (ReO) $cm^{-1}$. $^1H$ NMR ($CDCl_3$) δ 4.65 (d, J=16.5 Hz, 1 H, $CH_2CON$), 4.12 (m, 4 H, $CH_2CH_3$, $CH_2CO$ and $CH_2CH_2NCO$), 3.98 (m, 1 H, $CH_2CH_2CH_2N$), 3.56 (m, 1 H, $CH_2CH_2CH_2N$), 3.36 (m, 1 H, $SCH_2CH_2NCH_2CO$), 3.21 (m, 3 H, $CH_2CH_2NCOCH_2NCH_2$), 2.85 (dd, J=13.5 and 4.2 Hz, 1 H, $SCH_2CH_2NCH_2CO$), 2.29 (t, J=7.2 Hz, 2 H, $CH_2COO$), 1.79 (m, 2 H, $CH_2(CH_2)_{13}COO$), 1.60 (m, 1 H, $SCH_2CH_2NCH_2CO$), 1.20-1.10 (m, 25H, $(CH_2)_{12}CH_2COOCH_2CH_3$). $^{13}C$ NMR ($CDCl_3$) δ 187.10 and 173.90 (CO), 67.05, 63.95, 63.87, 60.11, 59.77, 47.76, 38.81, 34.35, 29.66, 29.55, 29.53, 29.40, 29.34, 29.21, 29.19, 29.10, 26.75, 24.94, 23.59 ($CH_2$), 14.22 ($CH_3$). MS m/z 676 and 674 ($M^+$).

In summary, the present invention has following advantages:
1. A method for synthesis of $H_3LMN$ series compounds applied to radiation therapy for liver cancer according to the present invention uses a $N_2S_2$ ligand having a tertiary amine, an amide and two thiols binding with Tc or Re to be used as therapeutic agents for liver cancer.
2. The ligand for synthesis of $H_3LMN$ series compounds contains only three free protons and reacts with $MO^{3+}$ (M=Tc or Re) to form electrically neutral complexes applied to radiopharmaceuticals.
3. The thiol group of a precursor of $H_3LMN$ series compounds is protected by the $CPh_3$ from being oxidized. Once the thiol group is oxidized, the precursor is unable to react with Tc or Re to form complexes. The precursor is with stable chemical properties that make it more convenient for storage.
4. The protecting group for thiol-$CPh_3$ is released easily during complex reactions with Tc or Re and there is no need to remove the protecting group in advance.
5. The precursor of the present invention is to bind with a long chain alkyl group such as a tetradecyl group, a hexadecyl group, or hexadecyl carboxylic acid ethyl ester so as to make the Re complexes have high lipophilicity and become soluble in lipiodol.
6. The method of present invention increases retention of $H_3LMN$ series compounds in liver tumor cells. Moreover, the long chain alkyl group improves lipophilicity of MO—$H_3LMN$ and solubility in lipiodol so as to enhance drug effect and retention in hepatoma cells.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:
1. A method of manufacturing $H_3LMN$ compounds having the structural formula

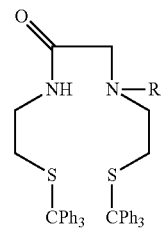

wherein R is selected from the group consisting of $(CH_2)_{13}CH_3$, $(CH_2)_{15}CH_3$ and $(CH_2)_{15}COOC_2H_5$, used as a precursor for the production of radioactive agents for treatment of liver cancer, comprising the steps of:
obtaining 2-[(triphenylmethyl)thio]ethylamine by a reaction between 2-thioethylamine hydrochloride and $CPh_3$;
obtaining N-[2-((triphenylmethyl)thio)ethyl] chloroacetamide by a transamidation reaction between 2-[(triphenylmethyl)thio]ethylamine) and chloroactyl chloride under existence of triethylamine;
producing an amine-amide-thiol ligand-N-[2-((triphenylmethyl)thio)ethyl] [2-((triphenylmethyl)thio) ethylamino]acetamide by a reaction between 2-[(triphenylmethyl)thio]ethylamine and N-[2-((triphenylmethyl)thio)ethyl] chloroacetamide; and
obtaining the $H_3LMN$ compounds having the formula

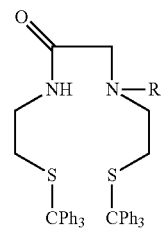

wherein R is selected from the group consisting of $(CH_2)_{13}CH_3$, $(CH_2)_{15}CH_3$ and $(CH_2)_{15}COOC_2H_5$ by a reaction of N-[2-((triphenylmethyl)thio)ethyl] [2-

((triphenylmethyl) thio)ethylamino]acetamide with 1-bromotetradecane, 1-bromohexadecane and ethyl 16-bromo-hexadecanoate, respectively.

2. The method as claimed in claim 1, wherein the method further includes reactions of $MO^{3+}$ and $H_3LMN$ and a step of reacting $MO^{3+}$ with $H_3LMN$ to produce electrically neutral complex-MO-$H_3LMN$.

3. The method as claimed in claim 2, wherein M of the $MO^{3+}$ is Tc-99, Tc-99 m, Tc-95 m, Re-186 or Re-188.

4. The method as claimed in claim 2, wherein triethyamine is used as an acid scavenger and the reaction is carried out in methanol solution.

5. The method as claimed in claim 1, wherein in the step of the reaction between 2-thioethylamine hydrochloride and $CPh_3$, triphenylmethanol is used as a reagent and boron trifluoride diethyl ether complex is a catalyst.

6. The method as claimed in claim 1, wherein in the step of obtaining N-[2-((triphenylmethyl)thio)ethyl] chloroacetamide by a transamidation reaction between 2-[(triphenylmethyl)thio]ethylamine) and chloroactyl chloride under existence of triethylamine, chloroactyl chloride is used as a reagent and the reaction is carried out in anhydrous dichloromethane solution.

7. The method as claimed in claim 1, wherein in the step of reaction between 2-[(triphenylmethyl)thio]ethylamine and N-[2-((triphenylmethyl)thio)ethyl] chloroacetamide, triethyamine is used as an acid scavenger and the reaction is carried out in anhydrous dichloromethane solution.

8. The method as claimed in claim 1, wherein in the step of the reaction of N-[2-((triphenylmethyl)thio)ethyl] [2-((triphenylmethyl) thio)ethylamino]acetamide with 1-bromotetradecane, 1-bromohexadecane and ethyl 16-bromo-hexadecanoate respectively KOH is used as an acid scavenger and the reaction is carried out in acetonitrile solution.

* * * * *